United States Patent
Pfeiffer et al.

(10) Patent No.: US 9,347,768 B1
(45) Date of Patent: May 24, 2016

(54) IN LINE ELLIPSOMETER SYSTEM AND METHOD OF USE

(75) Inventors: Galen L. Pfeiffer, Lincoln, NE (US); Blaine D. Johs, Lincoln, NE (US); Brian D. Guenther, Lincoln, NE (US); Martin M. Liphardt, Lincoln, NE (US); Jeffrey S. Hale, Lincoln, NE (US)

(73) Assignee: J.A. WOOLLAM CO., INC, Lincoln, NE (US)

( * ) Notice: Subject to any disclaimer, the term of this patent is extended or adjusted under 35 U.S.C. 154(b) by 214 days.

(21) Appl. No.: 13/385,761

(22) Filed: Mar. 6, 2012

Related U.S. Application Data

(60) Provisional application No. 61/464,582, filed on Mar. 7, 2011.

(51) Int. Cl.
| | |
|---|---|
| *G01J 4/00* | (2006.01) |
| *G01B 11/14* | (2006.01) |
| *G01J 3/02* | (2006.01) |
| *G01J 1/02* | (2006.01) |
| *G01N 21/01* | (2006.01) |

(52) U.S. Cl.
CPC ............... *G01B 11/14* (2013.01); *G01J 1/0242* (2013.01); *G01J 3/0278* (2013.01); *G01N 21/01* (2013.01)

(58) Field of Classification Search
CPC ................................ G01B 11/14; G01B 11/26

USPC ....................................................... 356/238.2
See application file for complete search history.

(56) References Cited

U.S. PATENT DOCUMENTS

| | | | | |
|---|---|---|---|---|
| 3,563,365 | A * | 2/1971 | Loberg ........................ | 198/790 |
| 6,108,091 | A * | 8/2000 | Pecen et al. .................. | 356/630 |
| 6,369,882 | B1 * | 4/2002 | Bruner et al. ................. | 356/73 |
| 7,505,134 | B1 * | 3/2009 | Johs et al. .................... | 356/369 |
| 7,872,751 | B2 | 1/2011 | Liphardt et al. ............. | 356/364 |
| 8,259,297 | B1 * | 9/2012 | Yarussi ........................ | 356/326 |
| 2002/0037462 | A1 * | 3/2002 | Ogata et al. ................... | 430/30 |
| 2002/0110218 | A1 * | 8/2002 | Koppel et al. ................. | 378/86 |
| 2008/0192987 | A1 * | 8/2008 | Helgason et al. ............. | 382/109 |
| 2009/0103093 | A1 * | 4/2009 | Liphardt ............... | G01N 21/01 356/369 |
| 2009/0299154 | A1 * | 12/2009 | Segman .............. | A61B 5/0059 600/301 |
| 2010/0204820 | A1 * | 8/2010 | Finarov et al. ............... | 700/213 |
| 2011/0019190 | A1 * | 1/2011 | Sakai ................ | G01N 21/3563 356/365 |
| 2011/0109906 | A1 * | 5/2011 | Liphardt ............... | G01N 21/01 356/400 |

* cited by examiner

*Primary Examiner* — Kara E Geisel
*Assistant Examiner* — Hina F Ayub
(74) *Attorney, Agent, or Firm* — James D. Welch

(57) ABSTRACT

A system for monitoring, in real time, relatively large samples as they are caused to pass by an ellipsometer or the like system, and method of its use.

6 Claims, 1 Drawing Sheet

IN LINE ELLIPSOMETER SYSTEM AND METHOD OF USE

This Application Claims Benefit of Provisional Application 61/464,582 Filed Mar. 7, 2011.

TECHNICAL FIELD

The present invention relates to systems and methods for monitoring samples using ellipsometry or the like, and more particularly to a system, and method of its use, for monitoring, in real time, relatively large samples as they are caused to pass by an ellipsometer or the like system.

BACKGROUND

It is known to, by applying ellipsometers, polarimeters, reflectometers and spectrophotometers, investigate samples using electromagnetic beams. Conventionally, samples investigated are relatively small and are mounted securely to a supporting stage. However, as demonstrated by recently issued U.S. Pat. No. 7,872,751, a sample can be relatively large, (ie. on the order of meters on a side as opposed to centimeters), and an ellipsometer can be mounted to a system which allows it to be moved and positioned so as to investigate different positions thereof. As a result a 751 Patent system is generally termed a Mapping System, as it allows constructing a map of characteristics of different positions on a sample. The 751 Patent, however, conforms to conventional practice by securing a relatively large sample to a similarly relatively large supporting stage. That is, the relatively large sample can not be moved during investigation thereof.

DISCLOSURE OF THE INVENTION

The present invention breaks with convention by providing a relatively large stage for supporting a relatively large sample which, in use, is caused to move over said stage while an ellipsometer, polarimeter, reflectometer or spectrophotometer is continuously applied to investigate parameters such as film thickness. The preferred embodiment, for instance, applies a conveyer system comprised of a plurality of "rollers", over which a sample with, for instance, a width dimension of upwards of a meter or two or more, and with a length dimension of perhaps many meters, moves. For instance, a sample could be the result of the manufacture of glass wherein the length of the sample can be many meters long with no certain restriction.

A problem with continuously monitoring a long sample as it moves over an ellipsometer, polarimeter, reflectometer or spectrophotometer system is that a "height" dimension, (eg. the distance between the surface of the sample being investigated and the investigating system), can vary with position on the sample. As the results of sample investigation vary substantially with said height distance, it is critical that said height distance be controlled in real time. That is, at each position of a moving sample being investigated, it is critical that the distance between the surface of the sample that a beam of electromagnetic radiation is caused to interact with, and at least one of the source of said beam and/or detector thereof, be quickly controlled to that intended before sample characterizing data is acquired. (It is noted that a preferred embodiment provides that the source and detector move as a group so that the same position on a sample is observed. However, the present invention can be practiced when only one of said source and detector is moved, with the drawback being that changing the height distance then changes the position on the sample which is subject to investigation). The present invention system therefore comprises a separate height monitoring sensor system, and a means for very quickly controlling said height.

A method of the present invention then involves:

a) providing a sample supporting stage which allows a sample to move thereover;

b) providing an ellipsometer, polarimeter, reflectometer or spectrophotometer system positioned with respect to said stage so that a beam of electromagnetic radiation produced by a source thereof can be directed to interact with a surface of a sample while it is caused to move over said stage, and enter a detector thereof;

c) providing a height monitoring and controlling system for quickly monitoring and controlling the distance between a surface of a sample being investigated and at least one of said source of said beam and a detector thereof;

d) causing a sample to move over said stage;

such that in use, at a multiplicity of positions of said moving sample, said height monitoring and controlling system sets the height between the surface of a sample being investigated and at least one of said source of said beam and a detector thereof; and at each said position on said moving sample said source causes a beam of electromagnetic radiation to interact with said sample and enter said detector, which detector produces data from which characteristics of said sample can be derived.

The present invention will be better understood by reference to the Detailed Description section of this Specification, in conjunction with the Drawings.

DETAILED DESCRIPTION

Figure 1:
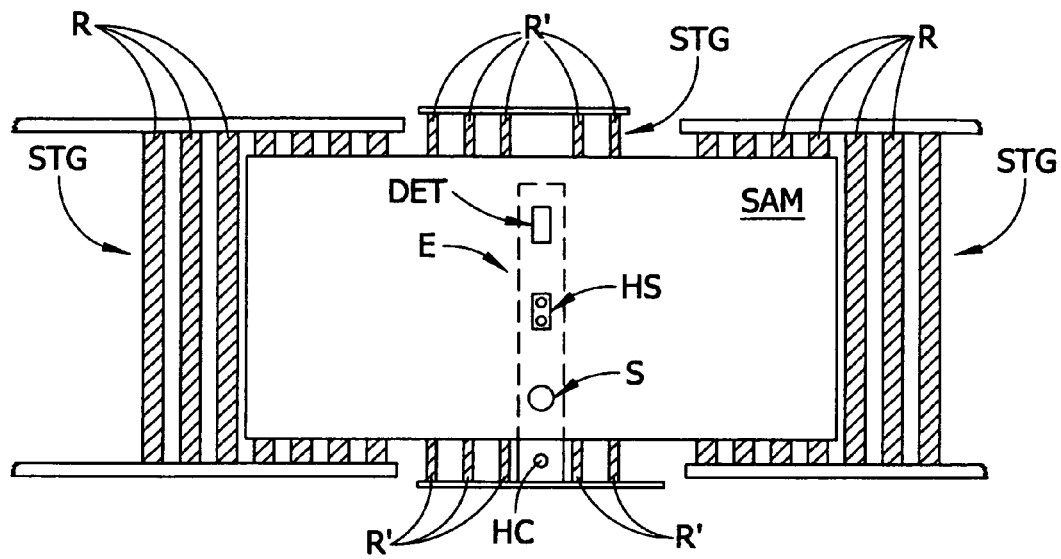
FIG. 1 shows a top view of the present invention system.
Figure 2:
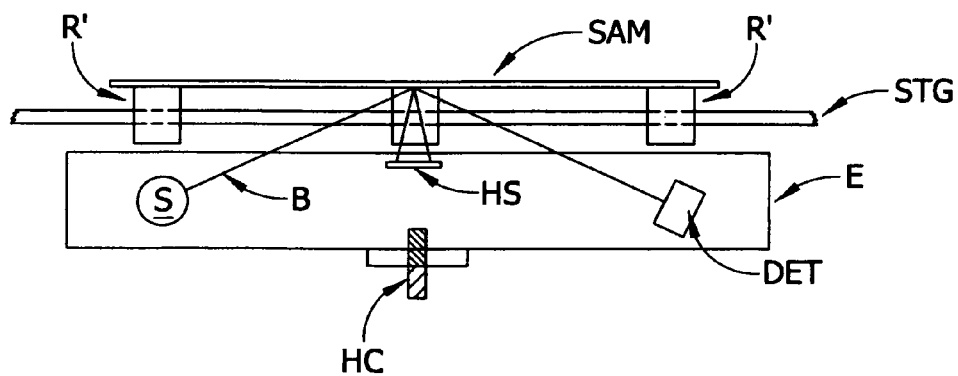
FIG. 2 shows a right side elevational view of the present invention system shown in FIG. 1.

Turning now to the Drawings, FIGS. 1 and 2 show top and right side elevational views, respectively, of a sample supporting stage (STG) which allows a sample (SAM) to move thereover and an ellipsometer, polarimeter, reflectometer or spectrophotometer system (E) positioned with respect to said stage (STG) so that a beam (B) of electromagnetic radiation produced by a source (S) thereof can be directed to interact with a surface of a sample (SAM) while it is caused to move over said stage (STG), and enter a detector (DET) thereof. Further, a height monitoring and controlling system (HS) for quickly monitoring, and controlling, the distance between a surface of a sample (SAM) being investigated and at least one of said source (S) of said beam (B) and a detector (DET) thereof, is shown.

It is noted that the stage (STG) is demonstrated as comprising rollers (R) (R'). This arrangement is particularly well suited to application where a very long moving sample is to be monitored.

It is also noted that the ellipsometer (E) is shown to be positioned below the sample (SAM) in FIGS. 1 and 2. This is demonstrative only and is not meant to, and does not limit the invention. That is, the ellipsometer (E) can alternatively be placed above the sample (SAM) in a functional manner.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of continuously monitoring and investigating a sample while it is moving linearly over a stationary stage, at a multiplicity of points on a surface thereof, comprising:
    while said sample is moving linearly over said stationary stage with respect to an ellipsometer, polarimeter, reflectometer, or spectrophotometer system that provides and directs an electromagnetic beam from a source thereof such that it interact with said surface of said sample and enters a detector, which detector acquires data from the entering beam,
    causing the position of an ellipsometer, polarimeter, reflectometer, or spectrophotometer to be detected and adjusted, in a direction substantially perpendicular to the direction of sample motion, so that the distance between said ellipsometer, polarimeter, reflectometer, or spectrophotometer source and a surface of said sample remains substantially the same at each and every point, of a multiplicity thereof on said sample, that is investigated while it is moving,
    to the end that deviations in data from an expected result are identified.

2. A method as in claim 1, in which the distance between the sample surface and ellipsometer, polarimeter, reflectometer, or spectrophotometer detector is simultaneously adjusted along with the ellipsometer, polarimeter, reflectometer, or spectrophotometer source.

3. A method as in claim 1, in which the distance between the sample surface and ellipsometer, polarimeter, reflectometer, or spectrophotometer source, as said sample is moving with respect to said ellipsometer, polarimeter, reflectometer, or spectrophotometer, is continuously sensed and adjusted.

4. A method as in claim 1, in which the ellipsometer, polarimeter, reflectometer, or spectrophotometer is positioned vertically below the sample, and in which said sample surface is on a lower side of said sample, and in which a beam of electromagnetic radiation produced by said source thereof approaches and reflects from said lower surface of said sample while said sample moves over said stage.

5. A method as in claim 4, in which said sample is the result of the manufacture of glass wherein the length of the sample is longer than it is wide and said sample movement is in a direction defined by said longer dimension.

6. A method as in claim 4 in which said stage is comprised of a plurality of rollers over which said sample moves, in a direction allowed by said rollers.

* * * * *